(12) United States Patent
Willing (10) Patent No.: US 6,278,517 B1
(45) Date of Patent: Aug. 21, 2001

(54) DEVICE FOR VISUALLY INSPECTING THE SURFACE CONDITION OF LARGE-DIMENSION SURFACES TO BE MATCHED

(75) Inventor: Achim Willing, Schesslitz (DE)

(73) Assignee: Dr. Ing. Willing GmbH (DE)

( * ) Notice: Subject to any disclaimer, the term of this patent is extended or adjusted under 35 U.S.C. 154(b) by 0 days.

(21) Appl. No.: 09/242,591
(22) PCT Filed: Aug. 21, 1997
(86) PCT No.: PCT/DE97/01870
  § 371 Date: Apr. 16, 1999
  § 102(e) Date: Apr. 16, 1999
(87) PCT Pub. No.: WO98/08078
  PCT Pub. Date: Feb. 26, 1998

(30) Foreign Application Priority Data

| Aug. 22, 1996 | (DE) | 196 33 806 |
| Oct. 29, 1996 | (DE) | 196 44 907 |
| Dec. 5, 1996 | (DE) | 196 50 469 |
| Jan. 4, 1997 | (DE) | 197 00 215 |

(51) Int. Cl.⁷ .................................. G01N 21/00
(52) U.S. Cl. ......................... 356/237.2; 356/446
(58) Field of Search .................. 356/371, 376, 356/237.1, 237.2, 446

(56) References Cited

U.S. PATENT DOCUMENTS

| 4,918,321 | 4/1990 | Klenk et al. . | |
| 5,414,518 | 5/1995 | Yazejian . | |
| 5,436,726 | 7/1995 | Ventura et al. . | |
| 5,636,024 | * 6/1997 | Crookham et al. | 356/371 |
| 5,686,987 | * 11/1997 | Hewitt et al. | 356/237 |
| 5,726,705 | * 3/1998 | Imanishi et al. | 356/371 |
| 6,088,093 | * 7/2000 | Greenberg | 356/237.3 |

FOREIGN PATENT DOCUMENTS

| 38 13 239 A1 | 11/1989 | (DE) . |
| 40 12 372 A1 | 10/1991 | (DE) . |
| 195 34 145 A1 | 4/1996 | (DE) . |
| 0 286 994 | 10/1988 | (EP) . |
| 2 173 299 | 10/1986 | (GB) . |

* cited by examiner

Primary Examiner—Richard A. Rosenberger
(74) Attorney, Agent, or Firm—Marshall & Melhorn, LLC (57) ABSTRACT

This invention concerns a device for visually inspecting the surface condition of large-dimension surfaces to be matched, in particular painted bodywork, with substantially vertical and horizontal surfaces to be matched or painted surfaces. Provided at a lateral spacing from the object are vertically disposed luminous elements whose principal radiation direction, viewed in horizontal planes, is directed at an oblique angle to the substantially vertical surfaces to be matched. The luminous elements are protected against being looked at directly from an observation position (B), located in the space between the object (1) and the luminous elements at least from direction R2 of the normals of the vertical surface to be matched.

17 Claims, 12 Drawing Sheets

DEVICE FOR VISUALLY INSPECTING THE SURFACE CONDITION OF LARGE-DIMENSION SURFACES TO BE MATCHED

BACKGROUND OF THE INVENTION

1. Field of the Invention

The invention relates to a device for visually inspecting the condition of large-dimension surfaces to be matched, especially painted bodywork, with substantially vertical and horizontal surfaces to be matched.

2. Description of the Prior Art

From prior art, optical devices for assessing the color of small surfaces are known; however these devices cannot be used for assessing large surfaces, for example whole vehicle bodies in automobile manufacture. Furthermore, different illumination structures for recognizing surface faults are known, with which the person involved has to look directly into the lamp and is thus dazzled. Moreover, the known arrangements for recognizing surface faults cause shadows to be cast by the people working, whereby fault recognition is only possible at certain positions which differ greatly from one another. The known devices for recognising surface faults do not permit simultaneous recognition of colour faults.

The purpose underlying the invention therefore is a device for visually inspecting the surface condition of large-dimension surfaces to be matched, by means of which device it is possible to recognize both surface faults and colour faults on large-dimension areas, especially painted bodywork, the workers not being dazzled and no shadow being cast by the workers.

This purpose is fulfilled according to the invention by the characteristic features of the main claim.

The visual inspection of surfaces to be matched includes both the matching of color, color effects and gloss and the recognition of paint faults. The recognition of the different faults requires respectively specific relationships between the observation direction and the illumination direction, and the design of the environment is also of great importance. For color matching, for example, oblique incident light radiation connected with vertical observation is favorable, a low luminance of the space delimitation reflected on the glossy surface to be matched being important, since too sharply defined overlaid illumination structure or luminance of the space delimitation is imposed on the impression of color and the recognition of color differences is hindered. This means that the lights or lamps may not reflect on the surfaces to be matched.

On the other hand, for the recognition of surface faults, reflection of the lighting structure is advantageous since faults at the corresponding reflected light/dark boundaries become visible through an alteration of the course.

For the invention, the following relationships arise between beam paths and types of fault or visual tasks:

Beam paths with reflected illumination structure permit the recognition of surfaces which are marked by geometrical deformation of the observed surface. Moreover the assessment of gloss and the assessment of the effect of effects paints is made possible.

Beam paths without reflection of the illumination structure make possible the recognition and the comparison of colors as well as the recognition of surface faults which do not result in any geometrical deformation of the surface. Through alteration of the illumination and/or observation angles, likewise color effects become visible.

To distinguish the various beam paths, the glancing angle must be taken into account, this glancing angle being defined as the angle by which the angle of observation deviates on a directed reflection from the direction of the reflected light ray. According to the size of the glancing angle, two observation geometries thus arise:

Small glancing angles, for example approximately 15°, cause beam paths on which the illumination structure is reflected so that surface recognition is possible.

Large glancing angles, for example approximately 45°, prevent the reflection of an illumination structure, which is useful in color matching.

Taking into account the above realizations, the purpose underlying the invention is fulfilled in that a plurality of luminous elements are provided in a fixed relationship to the surface to be matched, whose principal radiation direction, with a vertical arrangement and viewed in horizontal planes, is directed at oblique angles to the surfaces to be matched, the luminous elements being provided with screening devices, which are effective in a direction between the principal radiation direction and the direction perpendicular towards the surface to be matched, in such a way that, at least in observation of the measurement from the angles close to the direction of the normals, no luminous parts of the luminous elements are reflected on same. The luminous elements are here so screened, that rays, which hit the luminous elements from directions of the normals of the surface to be matched and in an angle range around the normal, either directly or after reflection on the light-deflecting reflectors allocated to the luminous elements, hit light-absorbent screens.

Through the device according to the invention in which the luminous elements radiate at an oblique angle, preferably below 45°, onto the surfaces to be matched, both surface faults of every kind and color faults as well as further surface effects for example the sag in metallic paints, may be recognized, the observer, when matching the object, being located between said object and the luminous elements, and through changing his location and/or through changing the direction of observation, all the required beam paths and observation paths can be realized. The luminous elements are protected against being looked at directly from the direction of the normals of the surfaces to be matched and in an angle range around the normal against being looked at directly, and thus remain without light radiation in these directions. Dazzling of the observer and the overlaying of the observation field by illumination reflexes in the case of color inspection do not occur.

Through the measures quoted in the subordinate claims, advantageous developments and improvements are possible.

The surfaces to be matched can be disposed horizontally vertically but also at an angle. Under the term 'substantially vertical and horizontal surfaces to be matched' as they occur on painted bodywork, those surfaces should also be understood which are slightly curved, a corresponding adaptation of the illumination geometry being possible, if desired.

The quality of the matching of horizontal surfaces, for example roof surfaces on vehicle bodies, can be improved by ceiling illumination, which preferably radiates the light at an angle, and is screened advantageously from directions perpendicularly from below and in an angle range around this direction. The observation of the vertical surfaces, for example the side surfaces of the vehicle bodies, can in the region close to the floor be improved by floor lights shining upwards, especially in an alignment transversely to the surface to be observed. The floor and ceiling luminous elements can be replaced by mirrors on the floor or ceiling to continue the illumination geometry of the side walls.

In the simplest case, according to the invention, the light distribution and shading of the illumination arrangement can be realised by a luminous wall or a plurality of individual lights, possibly already with bundled light distribution, of which perpendicular lamellae, aligned substantially parallel to the desired principal radiation direction, are disposed so closely beside one another that looking directly in an angle region around the normal of the perpendicular surface to be matched is no longer possible.

Through configuration of the luminous elements as lights with a reflector which preferably has a uniaxial curvature, and which bundles the light of one or more elongate lamps disposed parallel to the reflector axis, preferably fluorescent lamps, in planes transversely to the lamp axis, a disc-shaped screen being disposed preferably parallel to the principal radiation direction running towards the lamp, an illumination device is made available with lights which have integrated dazzle-reduction devices and are of flat construction with high lamp efficiency. Moreover these lights can be inserted as individual modules.

Moreover the shielding can be improved in that a plurality of screens is arranged in the one reflector half parallel to the first screen.

Color matching is improved and made more variable in that at least the screen surfaces which face the reflector portion and on which the incident light rays reflect, are absorbent and neutral in color, for example black or grey, which results in a sufficient reduction in luminance to avoid dazzling and irritations during the matching.

A further reduction in the constructional depth of the lights results from the fact that the one reflector half, which is turned towards the observer, is cut away, the central screen then being able to represent the housing wall of the reflector. Furthermore it is advantageous to provide a light-collecting reflector around the lamp. This light-collecting reflector can here either send the light back into the lamp with the effect of a small basic dispersion of the system, but with lower efficiency, or can go round the lamp with the effect of a larger basic dispersion and higher efficiency. In an advantageous development, the lights may be dimmed, a decline in the luminous flux of the lamps in the course of their service life being compensated for by the lamps being operated in the dimmed state and the dimming being withdrawn with an increasing drop in the luminous flux. Moreover, being dimmable has the advantage that, through a plurality of matching lights, a desired luminous intensity profile can be set on a surface to be inspected.

In advantageous manner, in order to reduce absorption losses on the outer surfaces to a minimum, reflective external reflectors which are directed to the lateral outer surfaces of the lighting housing may be attached and preferably be embodied as a continuation of the reflector of the light disposed beside it, the reflectors being able to be integrated at least partially into the housing shape.

On the other hand, however, these surfaces can also be realized in a neutral color with a low degree of reflection, in order to avoid reflexes.

BRIEF DESCRIPTION OF THE DRAWINGS

Embodiments of the invention, given by way of example, are shown in the drawing and are explained in the following description in greater detail. The figures show.

DESCRIPTION OF THE PREFERRED EMBODIMENTS

Figure 1:
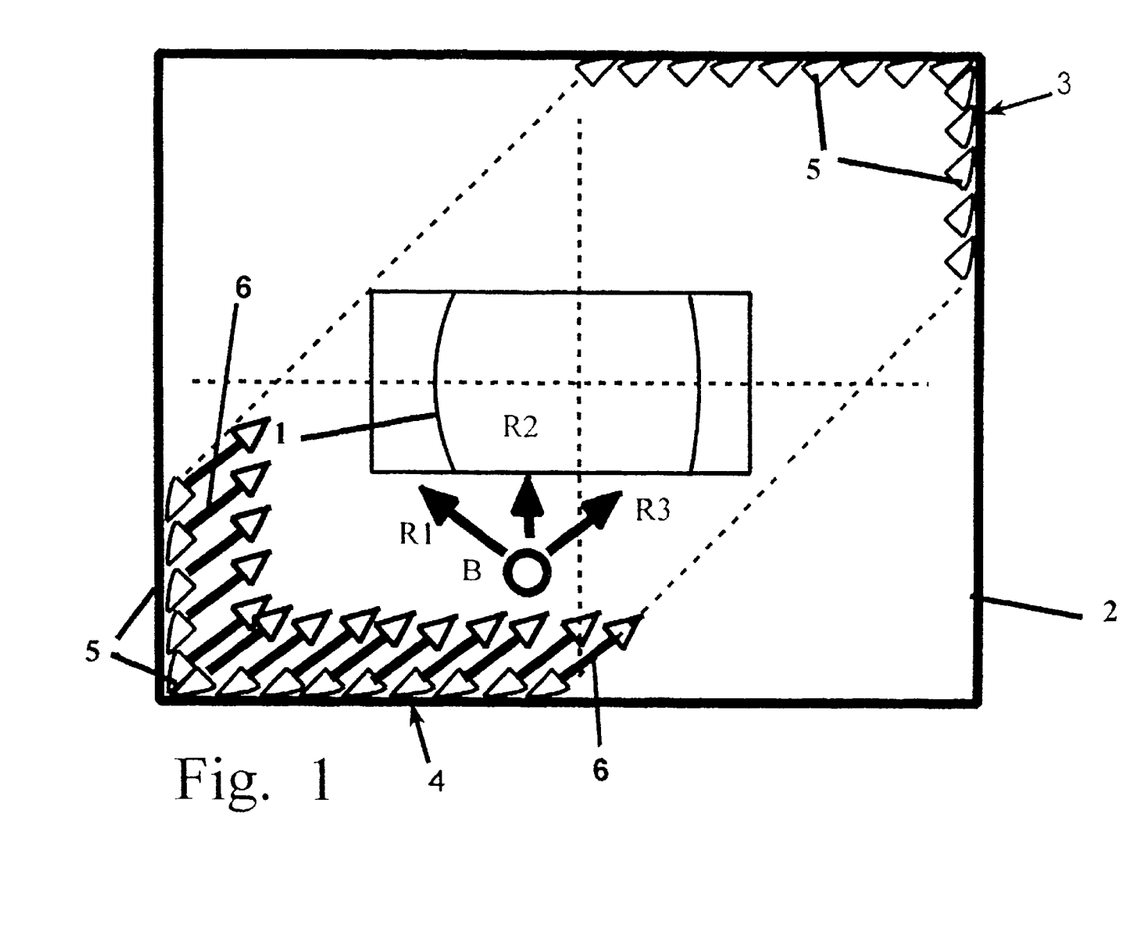
FIG. 1 a plan view of the device according to the invention with a vehicle body as the object to be matched, FIG. 2 a side view of the device according to the invention, FIG. 3 a plan view of a second embodiment of the device according to the invention, FIG. 4 a plan view of a third embodiment of the device according to the invention, FIG. 5 a side view of a horizontal surface, for example the roof of a vehicle body through a ceiling illumination, FIG. 6 side view of the illumination of the upper side surface of a vehicle body with ceiling lights, FIG. 7 a plan view of the lights with lamellae interposed as screening, FIG. 8 a section through a first light used in the invention with beam paths, FIG. 9 a section through a second embodiment of a light used, FIG. 10 a section through a further embodiment of a light with beam paths, FIGS. 11 and 12 a section through a further light with a plurality of screens of differing embodiment, FIG. 13 the surface of a screen with an absorption grid, FIG. 14 a section and a plan view of a light with parallel lamellae or discs disposed transversely to the lamp axis, FIG. 15 a section through two adjacent lights, FIG. 16 a section through a further embodiment of a light which is used in the invention, FIG. 17 a plan view of a part of the light arrangement used in the invention, in two embodiments, FIGS. 18 and 19 a section through a further embodiment of a light used in the invention, with different beam paths, FIG. 20 a section through a light such as is used as ceiling illumination in FIG. 5 and FIG. 6, and FIG. 21 a diagrammatic representation of an additional light used in the invention, in section, with different beam paths.
Figure 2:
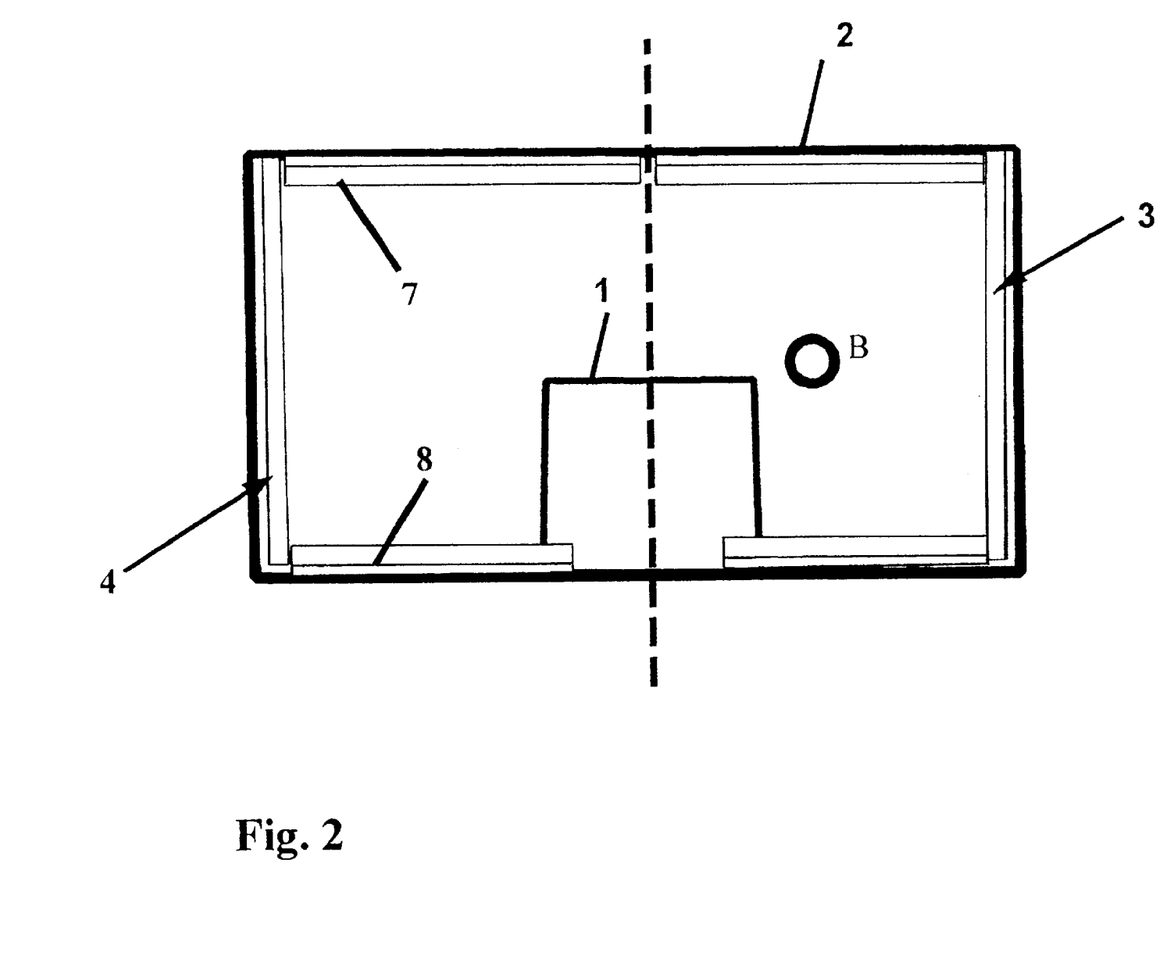

The device according to the invention is represented in the ground plan of a matching area 1 in FIG. 1 and correspondingly diagrammatically in a cross-section of the area in FIG. 2.

The object to be matched is, in the embodiment given by way of example, a completely painted vehicle body 1, which consists substantially of vertical and horizontal surfaces to be matched, slightly arched or curved surfaces also being included. The object is located in the middle of the area 2 and is illuminated by a lighting arrangement 3, 4 which is provided on the boundary walls of the area 2, a distance or space being left between the lighting arrangement 3, 4 which is at least sufficiently large for an observer B to be able to move about easily in the space.

The lighting arrangement 3, 4 consists of vertically disposed lights 5 which are disposed in this embodiment around the corners, in order to save space, the lighting arrangement 3 being disposed opposite the lighting arrangement 4. The lights 5, whose embodiments will be described later in detail, radiate at an inclined angle to the perpendicular surfaces of the object, the radiation direction being indicated by the arrows 6. The radiation angle is preferably 45°, the radiation direction being achieved in the simplest case by lamellae which are disposed at an angle of 45° parallel to, and at a spacing from, one another in front of a luminous wall or in front of any radiating lights 5. However these lamellae require a relatively large amount of space since they have to be sufficiently deep, such that special lights 5 with certain radiation characteristics are used, as will be described later.

The vertical partial surfaces of the object 1 are thus always illuminated obliquely and the lighting arrangements 3, 4 are so configured that looking directly from the direction of the normals to the perpendicular partial surface of the object is avoided. In FIG. 1, an observer B stands in the space or the path between the object 1 and the lighting arrangements 3, 4 and observes the side wall in different directions, which are indicated with the arrows R1, R2, R3. When the observer looks in direction R2, he sees the bodywork sidewall at a glancing angle of 45°, by which means it is possible to match the color. Direct dazzling by the opposite lighting arrangement 3, is prevented on account of the screening, for example by the lamellae not shown. Through the oblique incident light radiation, the observer does not cast shadows onto the visual field.

When the observer B looks in direction R1, because of the small glancing angle, the illumination structure, i.e. the structure of the lights, is reflected, whereby surface faults and structure effects of the bodywork surface can be recognized. By observing in direction R3, the observer B can recognize further surface effects, for example sag.

If desired, matching both according to color and according to surface and structural faults can be carried out, the observer being located during the matching in vertical alignment between the object and the lighting arrangement.

In FIG. 2, the area according to FIG. 1 is shown in section, there being provided here in addition to the lateral lighting arrangements 3, 4 a lighting arrangement 7 on the ceiling and a lighting arrangement 8 on the floor. Through such additional lighting arrangements 7, 8, especially surface faults in the roof region and in the lower region of the bodywork can be better recognized this being true likewise for the bonnet and the boot lid or low-lying horizontal surfaces.

Figure 5:
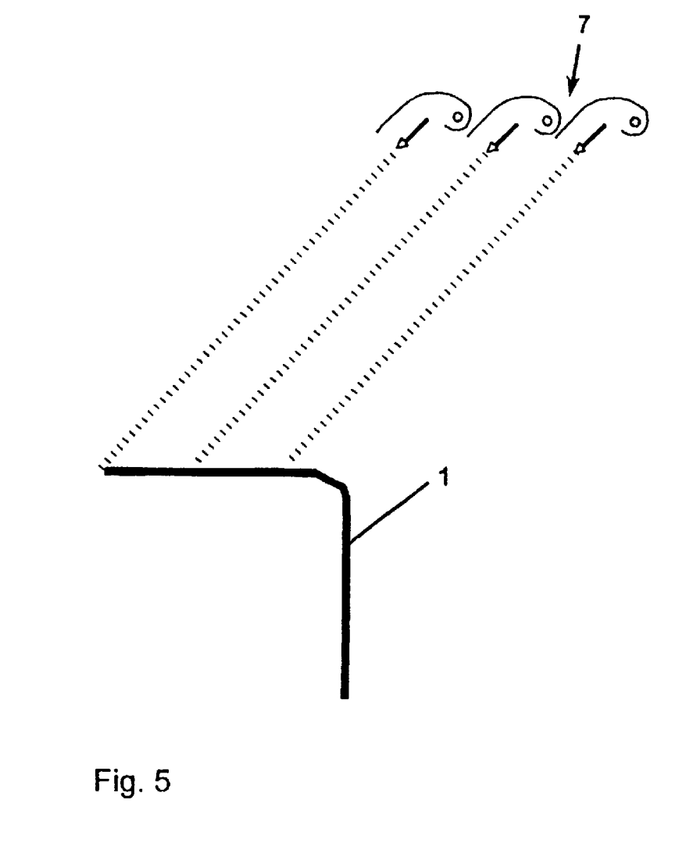
Figure 6:
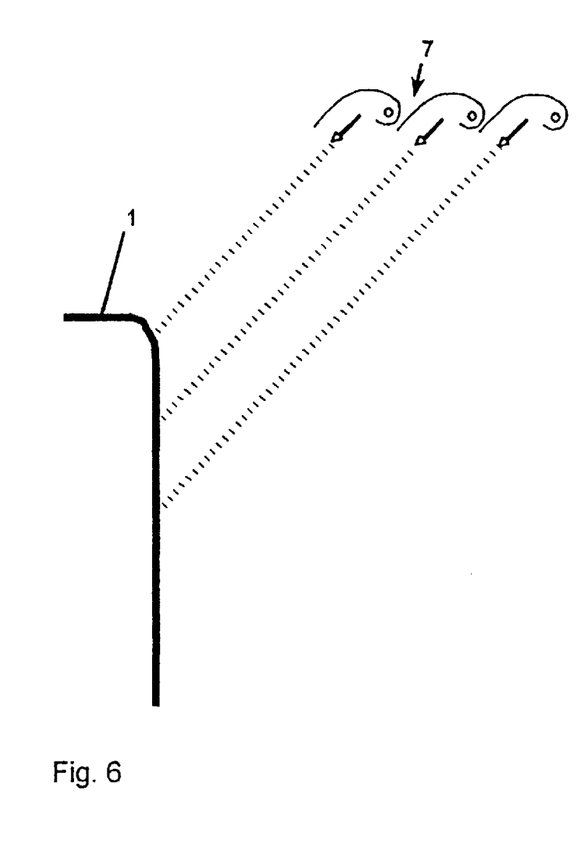

The lighting arrangement 7 consists either of deep radiating ceiling lights with a small radiation angle or of ceiling lights which radiate the light obliquely on one or both sides and are preferably screened from directions perpendicularly from below and in an angle range around this direction. In FIGS. 5 and 6 is shown diagrammatically a lighting arrangement 7 for the ceiling, the radiation direction likewise being 45° to the surfaces of the object 1. In FIG. 6, the ceiling lighting 7 is also used to observe the upper lateral surfaces. The lighting arrangement 8 on the floor consists of floor lights, which radiate the light obliquely on one or both sides and are preferably screened from directions perpendicularly from above and in an angle range around this direction. The lights of the lighting arrangement on the floor are expediently disposed transversely to the surface of the object 1.

Figure 7:
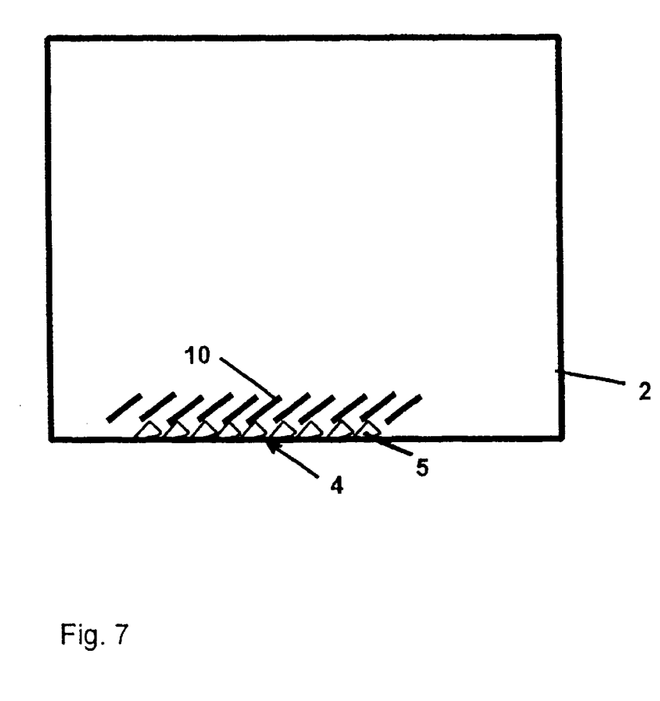
Figure 8:
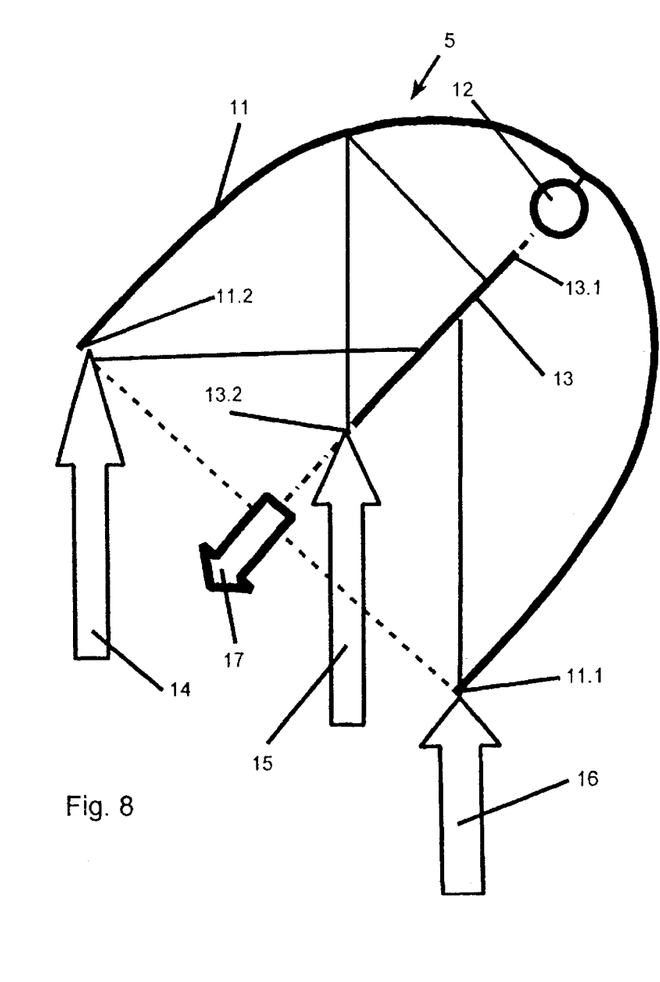

In another embodiment, the lighting arrangements 7, 8 on the ceiling and on the floor are replaced by mirrors which are disposed on the floor and on the ceiling, and which reflect the illumination geometry of the lateral lighting arrangements 3, 4. If necessary, the lighting arrangements 7 and 8 can also be omitted, the lateral lighting arrangements 3, 4 then taking over their function.

Figure 3:
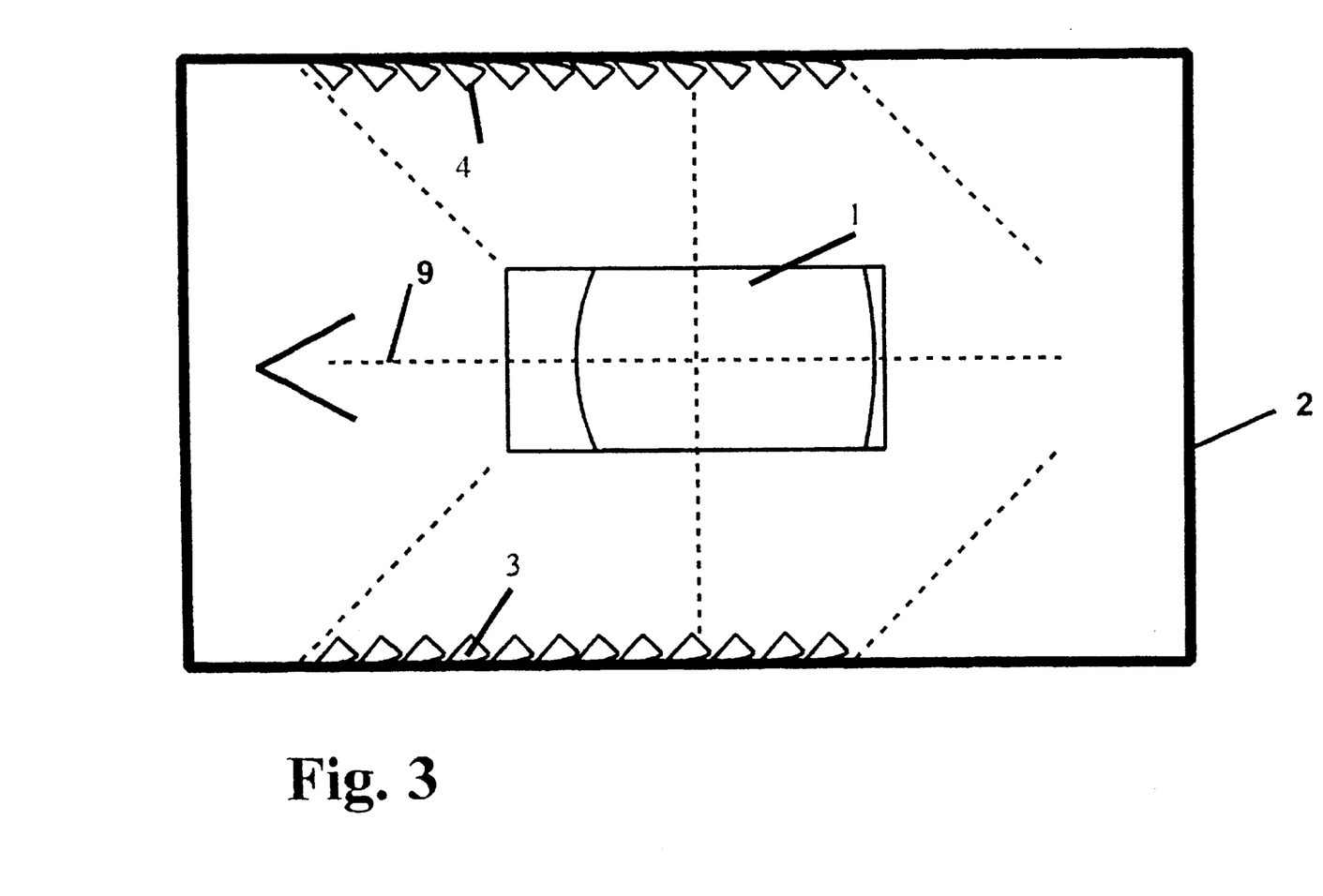

In FIG. 3 is shown a further embodiment with geometry different from that of FIG. 1, the lateral lighting arrangements 3, 4 being here only provided on opposite elongated side walls. The object 1, for example the bodywork, is here located on a conveyor belt 9, substantially the side surfaces of the object being matched. Such an arrangement is for example also suitable as assembly lighting.

Figure 4:
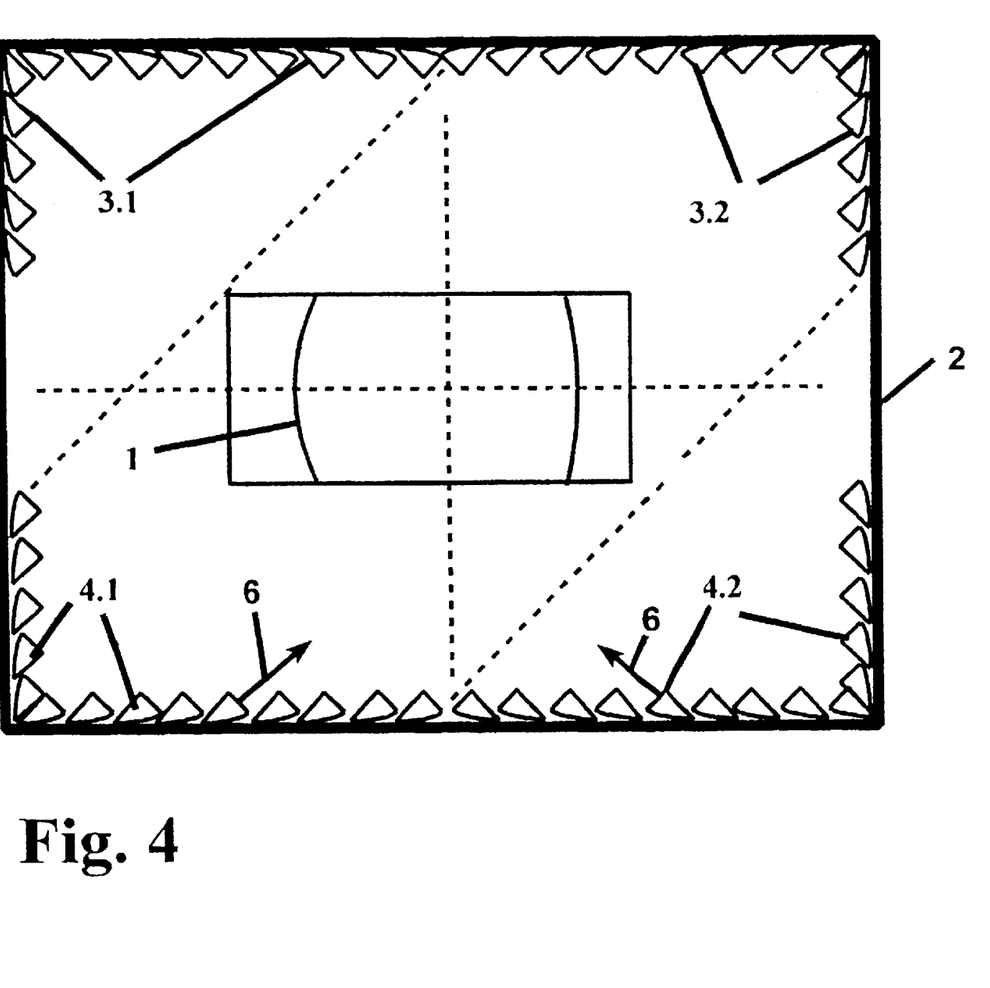

A further embodiment of the device according to the invention is shown in FIG. 4, the lighting arrangement 4 being divided up into lighting arrangements 4.1 and 4.2 and correspondingly the lighting arrangement 3 being divided into the lighting arrangements 3.1 and 3.2. Respectively the lights 5 of the lighting arrangements 4.1 and 4.2 or 3.1 and 3.2 radiate in radiation directions 6, which are vertically on top of one another, but both at an angle of approximately 45° to the vertical surface of the object 1. In this arrangement, the matching can be carried out right round the object, the vertical sections being able to be illuminated respectively from two directions in succession or simultaneously, in order to reduce, with simultaneous illumination, color effects which depend on direction, and with separate illumination, to make all the effects recognizable.

It is perfectly possible for the perpendicular lighting arrangements 3, 4 to consist of lights which, measured in a horizontal plane, radiate obliquely on both sides, preferably below ±45° and which on the basis of their optical system or through a corresponding arrangement of lamellae are protected against looking directly from the direction of the normals of the perpendicular surfaces to be matched. In this case, through a change of the viewing direction, likewise beam paths with and without reflection of the illumination structure can be realized, however sag effects in metallic paintwork can no longer be recognized.

In the lighting arrangements 3, 4, the separation of light 5 and screening device by the lamellae 10 in FIG. 7 is expensive and makes it difficult to have variable solutions in which the illumination elements may be composed in modular fashion. Moreover, relatively large constructional depths arise which are disadvantageous. Therefore specially adapted lights should be used which are described below.

The geometric parameters for the dimensioning of the optical system of a light 5 arise from the observation of sample light rays, whose course is taken into account in the optical system. A light 5 with such a beam path is shown in FIG. 8. The light 5, which is shown in cross-section, consists of a reflector 11 with a uniaxial curvature, which is configured parabolic in this embodiment but can also be elliptical, or is composed of polygon lines, and of an elongate lamp 12, for example a fluorescent lamp, the reflector 11 bundling the light of the fluorescent lamp 12 in planes transversely to the lamp axis. The principal radiation direction of the light 5 is indicated by arrow 17, the principal radiation direction 17, as described above, being at an angle of approximately 45° to the perpendicular side surfaces of the object 1 to be matched. In order to protect the viewing direction of the observer B against the radiation of the light 5, over the whole height of the light 5, preferably in the vertical plane of symmetry of the reflector 11, there is disposed a screen 13 in front of the lamp 12. The depth of the reflector 11 is here matched to the width and position of the screen 13 in such a way that when looking obliquely in relation to the main radiation direction 17, preferably at an angle of below 45°, the lamp 12 can be seen neither directly nor after reflection via the surface of the reflector. The dimensioning of the optical system is therefore to be carried out in such a way that all the light beams in the direction of the observer positioned obliquely to the main radiation direction 17 are either caught directly by the screen 13 or after reflection on the reflector 11. To this end, the following conditions are to be observed which are explained in relation to the beam paths. A light ray 16, which enters the reflector obliquely to the principal radiation direction 17 on the front edge 11.1, must fall onto the screen 13 in front of the rear edge 13.1 of same. A light ray 15 from the same direction as light ray 16, which hits the reflector 11 past the front edge 13.2 of the screen 13, is reflected there and must hit the screen 13. A light ray 14 from the same direction as light rays 15 and 16 hits the front edge 11.2 of the reflector 11, is reflected there and must hit the screen 13. These beam paths are shown in FIG. 8. Through this measure is guaranteed that, from the described directions, the reflector always appears in the color of the screen—i.e. dark—so that neither the luminance of the lamp nor the ambient brightness which has penetrated the reflector radiates in directions 14, 15, 16.

With structured or faceted surfaces of the reflector 11, the light rays expand to light bundles, such that the screen 13 then has to be enlarged until all the light rays are caught by the screen 13.

When the above conditions are met, from the respective observation direction, viewing the surfaces of the lamp 12 is no longer possible either directly nor after reflection via the reflector surface.

Figure 13:
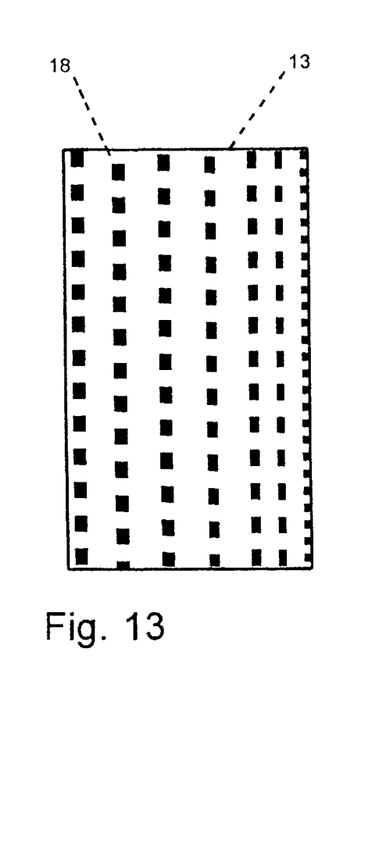

The surfaces of the screen 13 must on the one hand be so designed that the luminous flux falling directly from the lamp causes low brightness in the direction of the observer located at an angle to the principal radiation direction 17, yet on the other hand allows good quality of matching. This is given if both sides of the screen 13 are realized so as to be absorbent, and in the case of colour matching are designed in a neutral colour, for example black or grey. In order to cause even brightness distribution on the surface of the screen 13, which is turned away from the observer, in another embodiment, said screen is provided with a light-absorbent course grid, which is realized more heavily in regions close to the lamp. An absorption grid 18 of this sort is realized in FIG. 13. The left-hand side of the drawing plane is here the one which faces the lamp 12.

Figure 9:
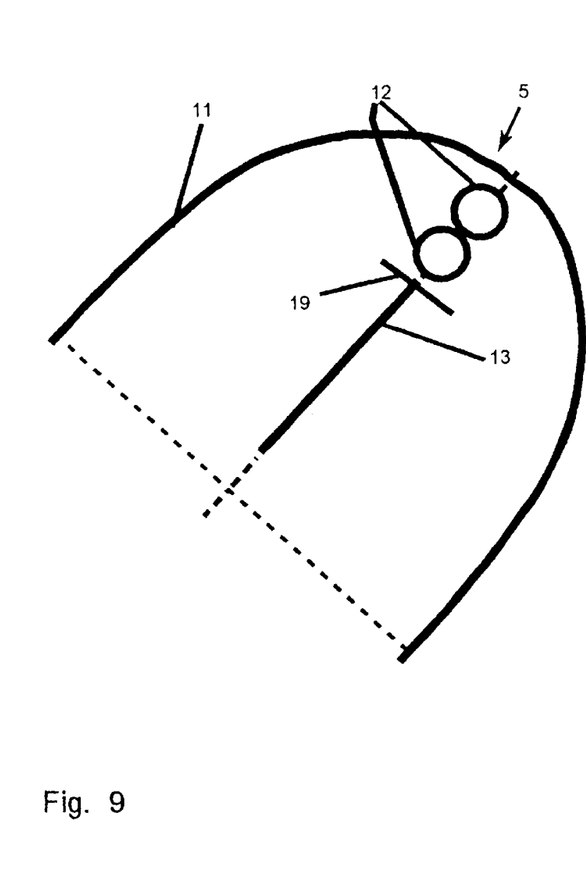

In FIG. 9 a further light 5 is shown in section, in which two lamps 12 are used to enlarge the radiated luminous flux. The lamps are covered by a reflector 19 disposed transversely to the screen 13 for even better removal of dazzle.

Figure 10:
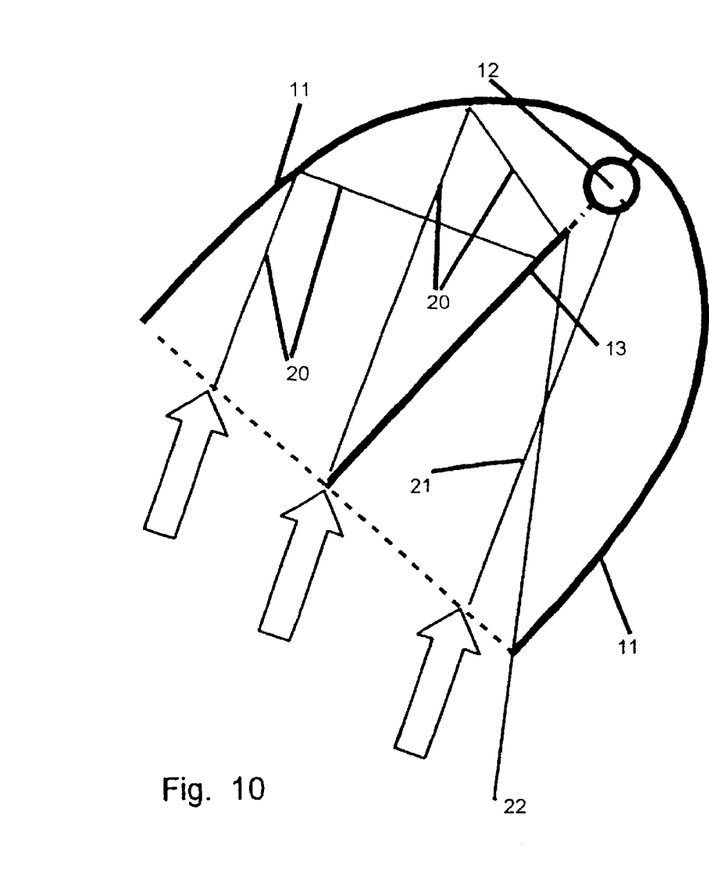

In FIG. 10 is represented a further embodiment of the light 5 with beam paths, here the screen 13, in contrast to FIGS. 8 and 9, extending as far as the front closing edge of the reflector 11.

It proves to be the case that when looking obliquely into the light 5 from directions outside the principal radiation direction, different screening arises for both sides of the reflector 11. These relationships are shown in FIG. 10, the sample light rays 20 simulating looking hitting the absorbent screen 13 after reflection on the upper side of the reflector in the plane of the drawing, whilst sample light rays 21 hit the lamp 12 from the same direction and thus light up. Sample light rays 22, which pass the front edge 11.1 of the reflector 11, hit the screen 13 and remain dark. Thus removal of dazzle for the reflector half which is further away from the observer B and uppermost in the drawing plane, is more favorable than the reflector half turned towards the observer and lowermost in the drawing plane. This recognition is taken into account in FIGS. 11 and 12, in which further screens 23 are disposed parallel to the screen 13 in the one reflector half, which for example protect the light rays corresponding to light ray 21 in FIG. 10. Their depth can be so configured that the light ray 22 serves as the boundary. The additional screens 23 which are aligned parallel to the central screen 13, in order to hinder the radiation of the reflector 11 as little as possible, can, corresponding to FIG. 12, be bent at their end turned towards the lamp 12, in order to increase their stability. Preferably the side facing the lamp of the bent portion 24 of the lamellae 23 is designed to be reflective, especially high-gloss, by which means the lamp efficiency is maximized. The central screen 13 can also be correspondingly bent.

In a further embodiment, not shown, all the screens 13, 23 are configured wedge-shaped with their wider end directed towards the lamp, and have the advantage of greater mechanical stability.

For the question of the surfaces, the same is true for the additional screens as for the central screen 13; however the sides of the screens 23 turned towards the lamp can be designed reflective, especially high gloss.

Figure 14:
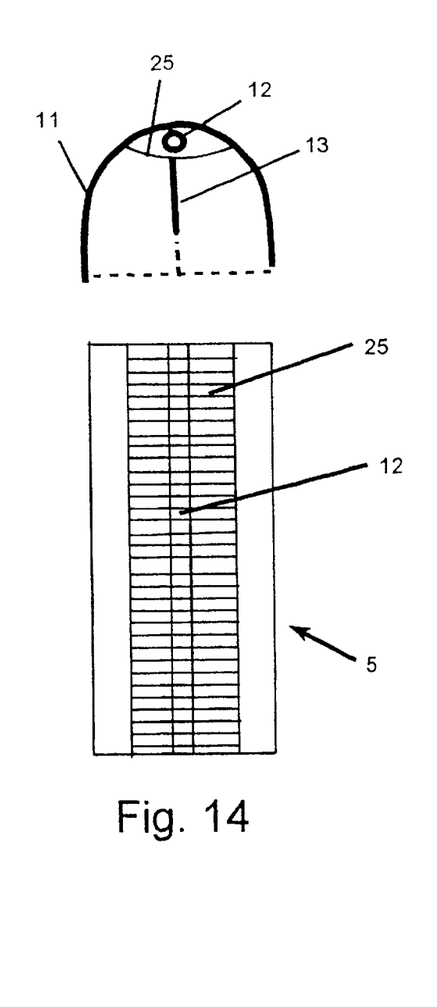

In FIG. 14 is represented a further a measure for optimizing the light radiation of the lights 5. On the elongate lamps 12, the bundling of the reflector 11 always relates to planes transverse to the lamp axis. Further optimization through bundling of the light rays in vertical planes as well can be achieved, if known light-absorbent lamellae or parabolically curved reflective lamellae which are disposed parallel to one another transversely to the lamp axis in front of the reflector or in the interior of the reflector. In order to direct especially large quantities of light onto the bodywork, such lamella can also be disposed obliquely with simultaneous alignment transversely to the lamp axis. This is also advantageous when lights are disposed perpendicular overhead, whose useful luminous flux is directed downwards. The lamella effect can be realized as prismatic discs or supplemented, as represented in FIG. 14. In this embodiment, the discs 25 are curved directly in front of the lamp 12 between the lamp and the screen 13, disposed over the whole height. In the upper portion of FIG. 14 is represented the section through the light 5 and in the lower portion, the side view. The discs 25 can be provided with triangular prisms running transversely to the lamp axis, disposed on the side turned towards the light exit surface, preferably at an acute angle of 120°, because these do not disturb the light distribution transversely to the lamp axis.

Figure 15:
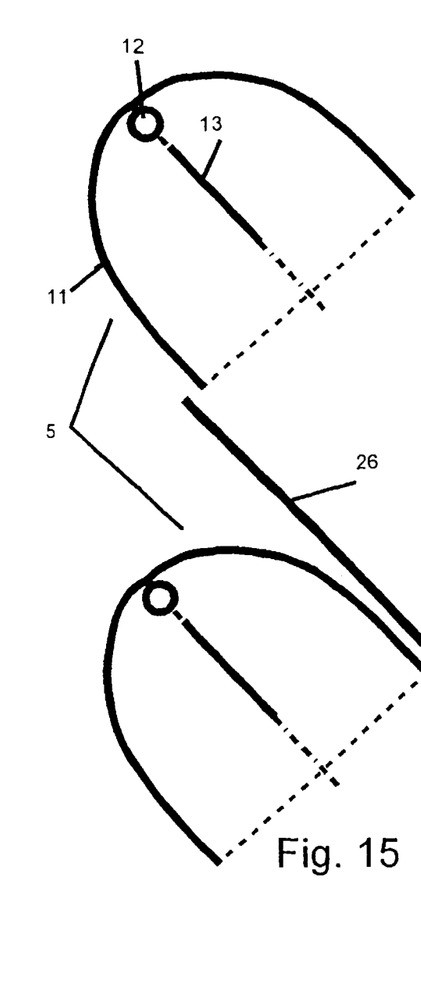

In FIG. 15, two lights 5 are disposed beside one another, their principal radiation direction again being 45° to the lateral surfaces of the object 1 to be matched. With the illumination of large surfaces, as shown in FIG. 1, a large number of lights of this kind 5 are placed beside one another as modular lights. In order to reduce to a minimum absorption losses on the outer surfaces of the lights 5, reflective reflectors 26 are disposed directed on the side outer surfaces of the lighting housing, which so to speak form the continuation of the inner reflector 11 of the light 5. These reflectors can be integrated at least partially into the housing shape.

If however, as in color matching, reflexes of the environment are to be suppressed, the surfaces 26 are preferably realized in a neutral color and light-absorbent, for example black or grey.

Figure 11:
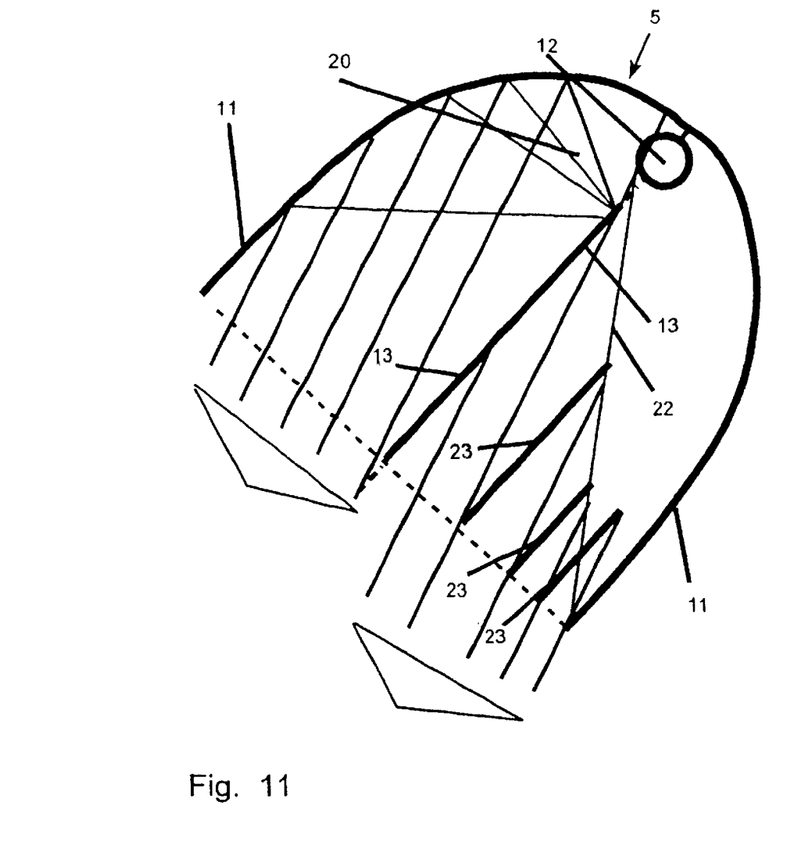
Figure 12:
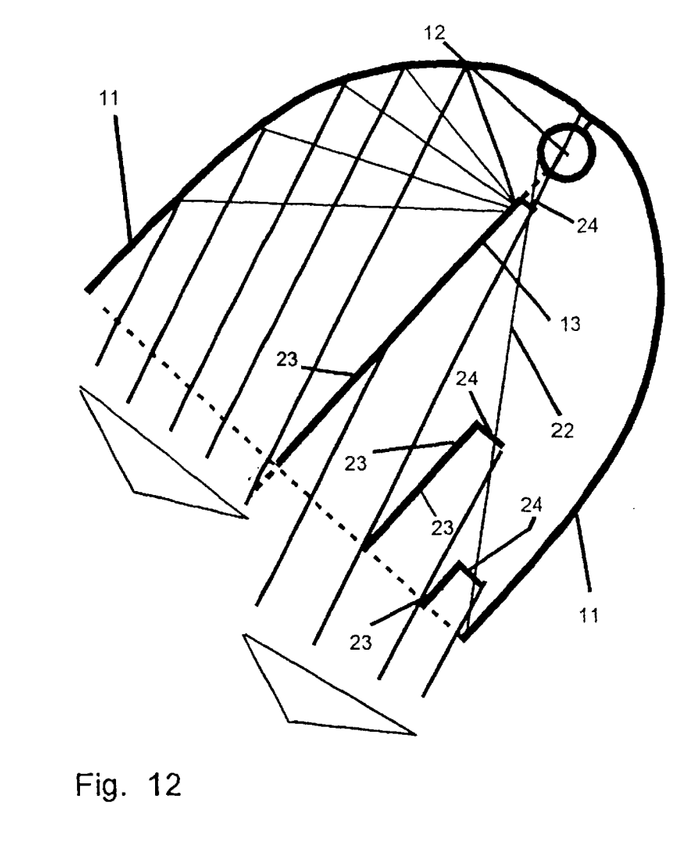

In FIGS. 11 and 12, a plurality of screens 23 is arranged in the reflector half facing the observer, to improve the screening effect, the dazzle reduction being considerably improved by this, however the lamp efficiency is also reduced. Thus in FIG. 16 as a continuation of the idea of removing dazzle, but with improved lamp efficiency, a further embodiment of the light 5 is represented with which the constructional depth of the whole lighting arrangement can be additionally reduced. Here the reflector half turned towards the observer is "cut away", and the light 5 consists of an arcuate reflector 27 which can be formed continuously like reflector 11, or is composed of flat or curved strips, and whose surface can be high-gloss or slightly structured in order to increase the evenness of the light radiation, a reflector portion 28, which is substantially in the shape of a circular arc, joining onto the portion which is curved in cross-section, and the lamp 12 being received in this portion 28 whose cross-section is in the shape of a circular arc. The screen 13 joins onto the end of the portion 28 which is in the shape of a circular arc, and simultaneously represents the boundary surface downwards. The reflector portion 28 whose cross-section is in the shape of a circular arc thus represents a light-collecting reflector, which sends the light back into the lamp with the effect of a small basic dispersion of the system but lower efficiency, or however conducts the light around the lamp with the effect of greater basic dispersion and higher efficiency. The reflector material is here preferably high-gloss with as high a reflection degree as possible of the directed reflection.

Figure 16:
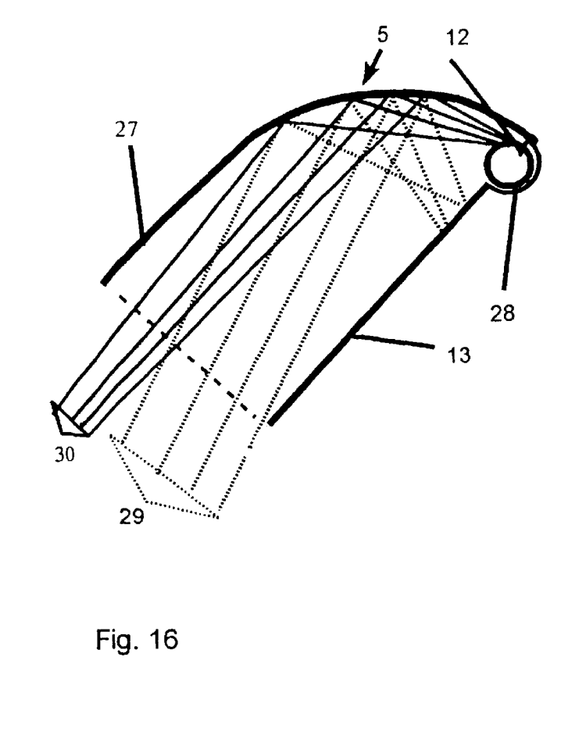

In FIG. 16 is represented a light 5 with an asymmetrical light distribution which is severely cut away on the side turned towards the observer and may radiate in any width on the side turned away from the observer, with various beam paths. The sample light rays from direction 29 meet the required conditions for screening, by hitting the screen 13, which is configured to correspond to the screen in the preceding embodiments. The direction of the sample light rays is outside the light distribution 30 of the reflector 1, determined by the light rays coming from the lamp 12. Looking directly onto the lamp 12 from directions towards which the outer side of the screen 13 faces, is not possible. The reflector portion 28 collects the lamp light and reflects it into the lamp, such that its average luminance is increased. In this case, the basic dispersion which arises from the size of the lamp 12 is maintained.

Figure 18:
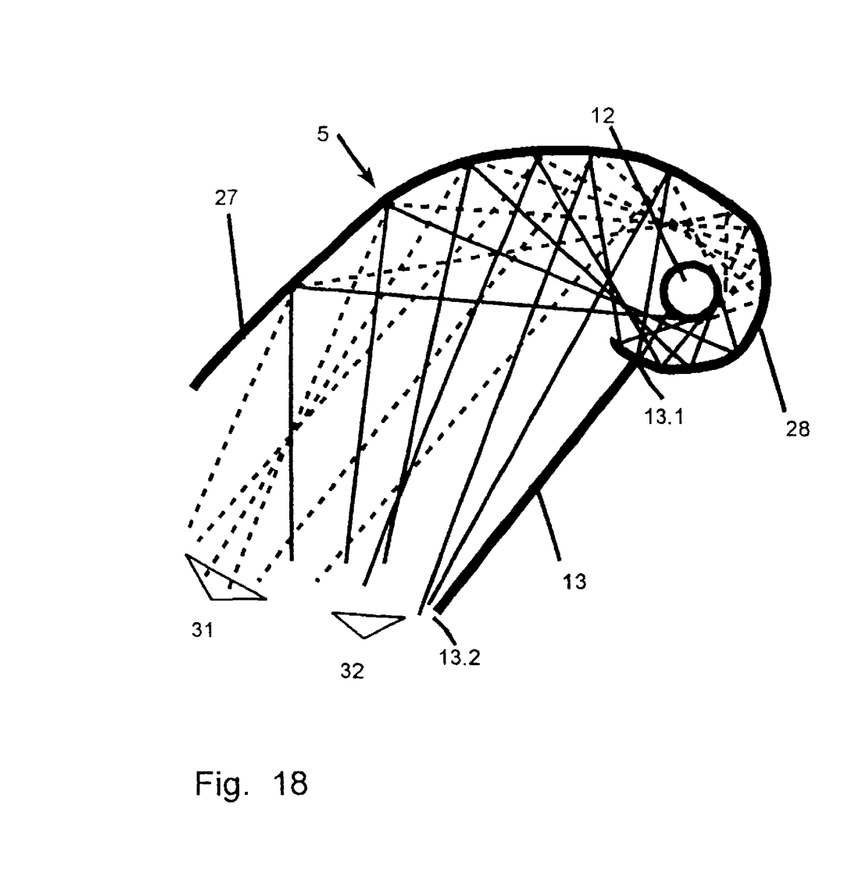
Figure 19:
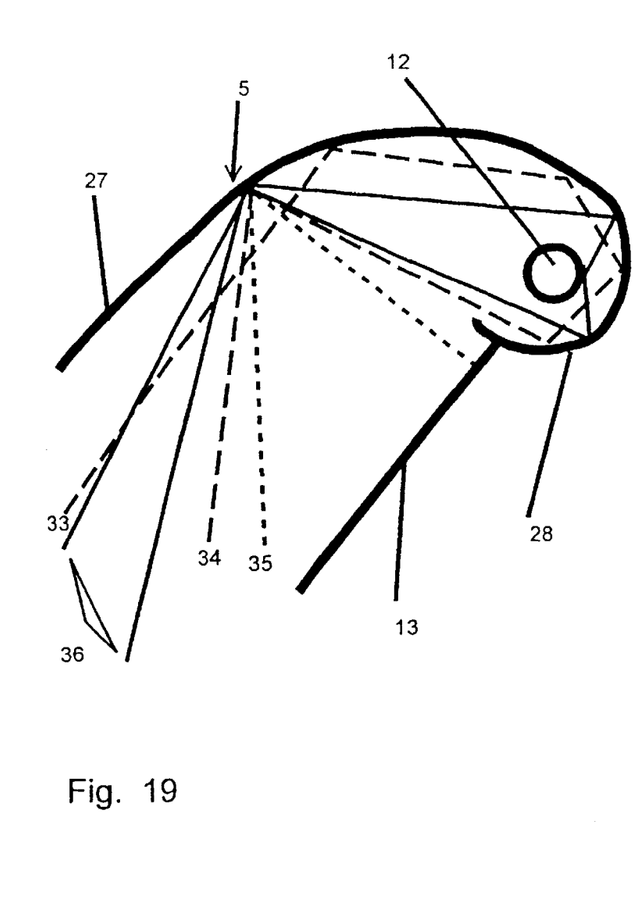

In FIG. 18 and FIG. 19 is represented a further embodiment in which the reflector portion 28 is at a greater distance from the lamp 12, by which means the lamp 12 is optically enlarged. In this case, the reflector portion 28 which is partially circular in cross-section is so shaped that light rays 31 which hit the reflector portion 28 in a certain region behind the lamp 12, and light rays 32 which hit it before the lamp 12 reach the lamp 12 after reflection. By this means, the lamp 12 is apparently enlarged and greater basic dispersion of the reflector is achieved. Since the light rays are not reflected back into the lamp, and thus cannot be absorbed, this reflector has greater efficiency. The form of the arcuate reflector portion 27 is expediently so determined that a closed illumination between 31 and 32 occurs, and preferably in such a way that all the light rays are reflected past the starting point 13.2 of the screen. The semi-circular reflector portion 28 is in turn preferably disposed so far around the lamp and drawn over the screen 13, that the screen 13 is not radiated by the lamp 12. The end edge 13.1 of the screen 13 can be disposed in any way in the shadow of the reflector portion 28, but should join onto it directly.

In FIG. 19 is shown another beam path, and the deflection effect for the light rays 33, 34 and 35 is shown. These light rays admittedly touch the reflector portion 28 which is semi-circular in cross-section, but are led out of the reflector portion 28 again without hitting the lamp 12, such that the sample light rays cannot assume the luminance of the lamp 12. The dark sample light rays 33, 34, 35 lie outside the light bundle 36.

In addition, a screen can be provided perpendicular to the surface of the reflector portion 28 between the latter and the lamp 12, so that the path beam is interrupted inside the light-collecting reflector portion 28. Through light-absorbent qualities of the additional screen, the removal of the dazzle from the light 5 is further improved. The lights 5 are closed preferably at least approximately transversely to the principal radiation direction 17 with closing discs, in order to prevent interfering reflections on the surface of the covering discs. Preferably such closing discs should be realized so as to be non-scattering. In order to achieve soft transitions between the light distributions of adjacent lights, it can be advantageous to realize the closing discs as slightly dispersing. In special cases, strong dispersion can be selected if the dazzle limitation is of lesser importance.

Figure 17:
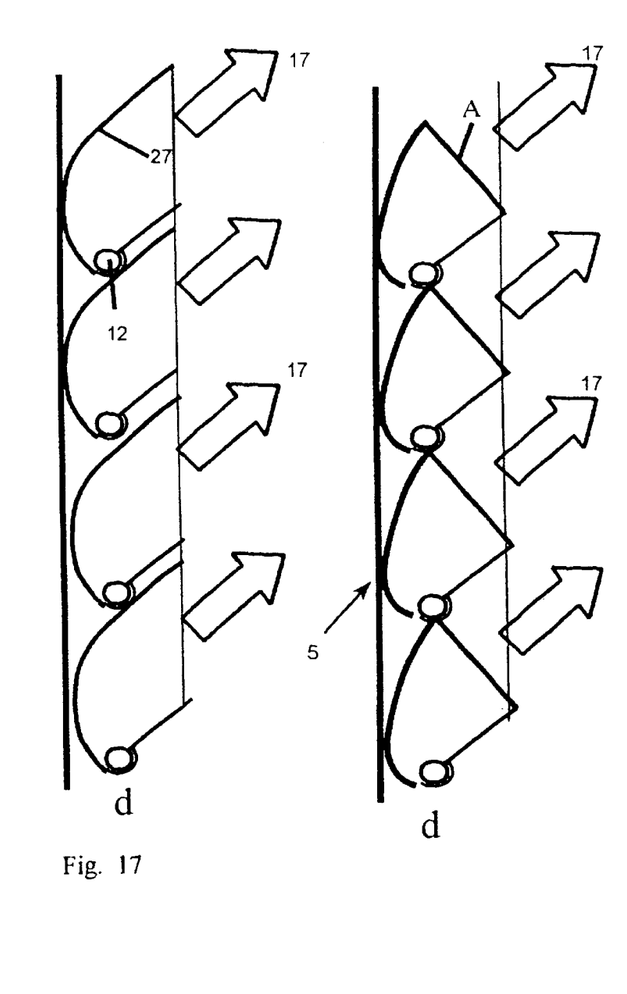

In FIG. 17 is disposed a plurality of lights 5 corresponding to FIGS. 16, 18, 19, which are lined up obliquely to one another, their principal radiation direction 17 being aligned at an angle of 45° to the surface to the matched. It can be recognized that the constructional depth d is only determined by "a" reflector half and is therefore small. Two embodiments are shown, with and without covering disc A.

Figure 20:
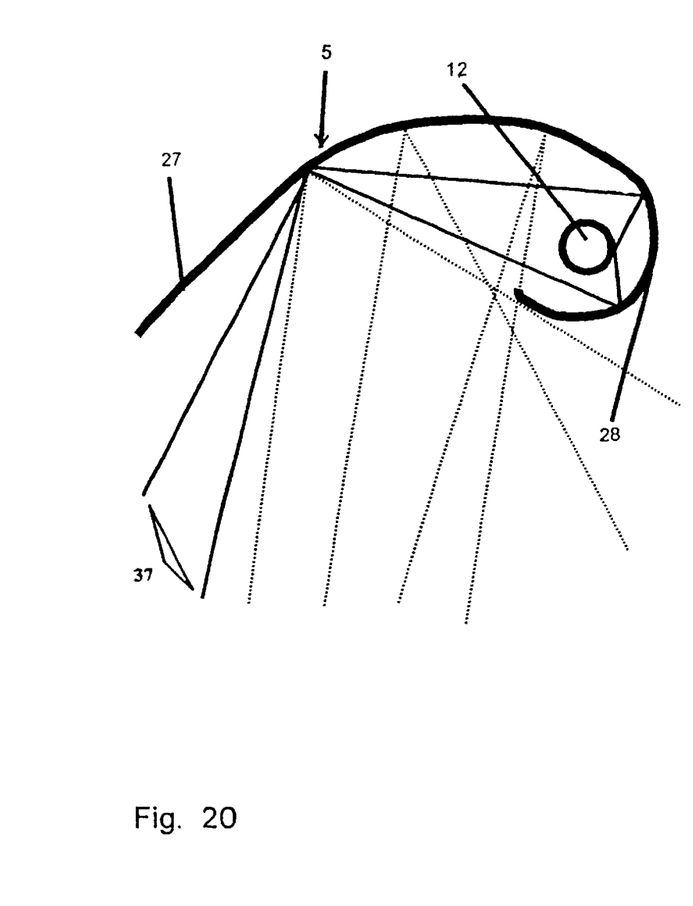

In FIG. 20 is represented a further embodiment of a light, in which the screen 13 is omitted, the reflection qualities being thus lessened and the environment being able to be reflected in the reflector. The light of the lamp 12 is radiated inside the light-radiating bundle 37, whilst the light rays shown in broken lines remain dark. It can be sensible to allow a corresponding light to follow on from the reflector portion 28 or 27 with mirror symmetry, and to use it for ceiling lighting in order to have light radiation on both sides.

Lights of this kind are especially suitable as ceiling lights, which are disposed laterally beside the bodywork or the surfaces to be matched, so that the reflection of the ambient brightness does not interfere. They are furthermore suitable for illumination in which color-matching is of subordinate importance or plays no part.

Figure 21:
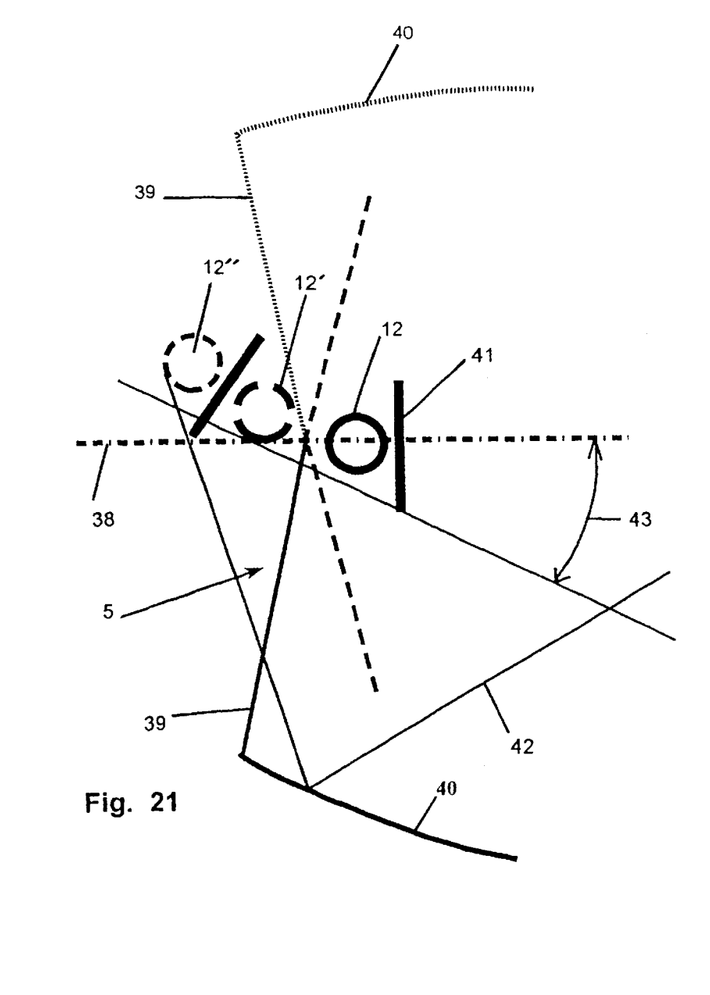

In FIG. 21 is represented a further embodiment of a light 5 in cross-section, which may be used for the lateral lighting arrangement 3, 4 in FIG. 1, if color matching is of subordinate or no importance. A reflector 39, 40 is provided which is designed symmetrically to the plane of symmetry 38, respectively one flat reflector portion 39 being disposed at an angle of approximately 75° to the plane of symmetry 38, followed by a slightly curved reflector portion 40. Another elongate lamp 12 is disposed on or in the plane of symmetry and is covered transversely to the plane of symmetry 38 by a screen 41 which is realized high-gloss on the side facing the lamp 12.

In FIG. 21, the reflections of the lamp 12 and of the screen 41 are represented as virtual light sources 12' and 12" and as a virtual screen 41'. The reflector portion 40 reflects a boundary ray 42 of the lamp 12 reflected first on the screen 41 and then on the reflector portion 39, i.e. of the virtual lamp 12", in directions greater than a deflection angle 43 of 30° to 40° to the plane of symmetry 38. The width of the reflector 39, 40 is chosen to be such that the lamp 12 and all the images 12', 12" only become visible at angles greater than the deflection angle 43.

The light 5 according to FIG. 21 is particularly suitable for fault recognition on shiny bodywork with simultaneous oblique, and therefore low in shadows, illumination of the working field and in particular of working fields moved on conveyor belts. They can also be used advantageously as built-in floor lights, perpendicular to the direction of conveying, and as ceiling lights. According to the required luminous intensity, they can be disposed both closely beside one another and also at a spacing.

Fluorescent lamps which have a suitable spectral light distribution are preferably used as lamps 12. Such lamps should be as similar as possible to the comparative natural light source, usually daylight. Fluorescent lamps are suitable if their so-called index of metamerism is greater than 0.7. What is disadvantageous about such lamps is their severe loss of luminous flux during their service life. For this reason, a control circuit and a dimming device are provided, via which device the lamps can be operated in the dimmed state, and which detects the drop which increases in the course of the service life and indicates this to the control circuit, by means of which the dimming is withdrawn. Via the dimming device it is also possible for a certain luminous intensity profile to be set for a plurality of lights, which is advantageous for a surface to be inspected.

All the lights described can be so configured that a plurality of reflectors or optical systems are disposed parallel in a housing directly beside one another or with a mutual spacing.

Moreover all the lights or reflectors can be so configured, for example respectively in mirror symmetry to one another, that they are suitable for a radiation of ±45°, by which means even illumination especially for assembly, for example on assembly lines, is achieved.

In the above description, in respect of the lamps 12, "elongate" lamps are mentioned, i.e. linear lamps. This term is also intended to cover substantially punctiform lamps with corresponding reflectors which are arranged in linear fashion. This results in the possibility of bundling the light distributions not just in one plane, for example the horizontal plane, but in all spatial directions.

The lights 5 described above can also be used for color matching and surface inspections, especially for small samples, for example in the laboratory, it then being unnecessary for the observer to be able to move between object or sample and lights.

For example, the sample can be illuminated at an angle of 45° and the observer views the sample from a general observation direction of 0°. Here, even with slight deviations of the observation direction, the sample remains dark for the observer as a result of the light distribution curve, described above, which has a sharp cut-off, i.e. there is direct dazzling. The lights can here shine from above or the side onto samples disposed horizontally, at an oblique angle or vertically, preferably at an angle of 45°, and the observer correspondingly views the sample from a direction perpendicular to the sample with angle deviations admissible for inspection.

What is claimed is:

1. A device for visually inspecting the surface condition of large-dimension surfaces to be matched, comprising a plurality of luminous elements are provided in a fixed relationship to the surface to be matched and whose principal radiation direction runs respectively at an acute angle to the surface to be matched, the luminous elements being provided with screening devices which are effective in a direction between the principal radiation direction and direction (R2) towards the surface to be matched, in such a way that no luminous parts of the luminous elements are reflected on the surface to be matched when it is observed from angles close to the direction (R2) of the normal.

2. Device according to claim 1, wherein the screening devices for the luminous elements are so configured that rays reflected from directions normal to the surface to be matched and in an angle range around this normal hit light-absorbent screens either directly or after being reflected on light-deflecting reflectors associated with the luminous elements.

3. Device according to claim 1, wherein light from the luminous elements cover a surface which is at least as large as the total surface to be matched.

4. A device according to claim 1, wherein the luminous elements shine on to the surfaces to be matched at an angle of roughly 45°.

5. A device according to claim 1, wherein the surfaces to be matched and the luminous elements are disposed substantially vertically at a mutual spacing, and the observation position (B) is located in the space between the surface to be matched and the luminous elements.

6. A device according to claim 1, wherein the luminous elements are configured as elongate lights having a light-deflecting reflector and having at least one lamp disposed parallel to the reflector axis, the reflector bundling the radiation in planes transversely to the lamp axis.

7. Device according to claim 6, wherein the reflector of the luminous element consists of a first reflector portion which bundles the light of the at least one lamp in a principal radiation direction, a second light-collecting reflector portion, disposed in the proximity of the lamp and partially around same, and an absorbent screen, located opposite the first reflector portion and aligned substantially parallel to the principal radiation direction, the first reflector portion and the second reflector portion merging into one another and the screen being disposed after the second reflector portion between the latter and the light exit surface.

8. A device according to claim 7, wherein the second reflector portion is disposed in the immediate proximity around or directly on the at least one lamp, in such a way that the substantial portion of the light of the lamp is reflected on same.

9. A device according to claim 7, wherein the second reflector portion is disposed at a spacing from the at least one lamp, in such a way that a substantial portion of the light of the lamp is reflected into the space immediately adjacent to said lamp.

10. A device according to claim 6, wherein the lights respectively have a symmetrically designed reflector made of two flat reflector portions disposed behind the lamp and running respectively at an angle towards same, and slightly curved reflector portions joining on to the other portions at their end remote from the lamp, a screen which is highly reflective on one side being disposed in front of the at least one lamp transversely to the plane of symmetry of the reflector.

11. Device according to claim 6, wherein the reflector of the luminous element consists of a first reflector portion which bundles the light of the at least one lamp in a principal radiation direction, a second light-collecting reflector portion, disposed in the proximity of the lamp and partially around same, and a light-scattering screen, located opposite the first reflector portion and aligned substantially parallel to the principal radiation direction, the first reflector portion and the second reflector portion merging into one another and the screen being disposed after the second reflector portion between the latter and the light exit surface.

12. A device according to claim 1, wherein the screening is configured as lamellae disposed obliquely in front of the luminous elements.

13. A device according to claim 1, wherein a disc-shaped first light-absorbent screen is arranged parallel to the principal radiation direction of the reflector in a direction towards the at least one lamp, in such a way that light rays hitting the reflector at oblique angles to the principal radiation direction are caught by the screen directly or after being reflected on the reflector surface.

14. A device according to claim 13, wherein at least one additional screen, preferably a plurality of same, is disposed at least in one portion of the reflector parallel to the first screen.

15. A device according to claim 1, wherein a screen is disposed in front of the lamp transversely to the principal direction of radiation.

16. A device according to claim 1, wherein the luminous elements may be realized by means of punctiform lamp arrangements.

17. A device according to claim 1, wherein the lights are connected to a dimming device, with which an illumination profile of the lighting arrangement may be set, the dimming device being a component of a control circuit with sensors for measuring the luminance of the lamps and the lamps being dimmed in such a way that, independently of the reduction in the luminous efficiency of the lamps caused by the length of their operation, the luminous flux of the lamps remains constant.

* * * * *